(12) United States Patent
Klepper (10) Patent No.: US 8,480,722 B2
(45) Date of Patent: Jul. 9, 2013

(54) TUBULAR DEVICE DELIVERING LIGHT AND RADIATION INTO A PATIENT

(76) Inventor: Mark Klepper, Austin, TX (US)

(*) Notice: Subject to any disclaimer, the term of this patent is extended or adjusted under 35 U.S.C. 154(b) by 496 days.

(21) Appl. No.: 12/661,551

(22) Filed: Mar. 19, 2010

(65) Prior Publication Data
US 2010/0241198 A1 Sep. 23, 2010

Related U.S. Application Data

(60) Provisional application No. 61/210,515, filed on Mar. 20, 2009.

(51) Int. Cl.
*A61N 5/06* (2006.01)
(52) U.S. Cl.
USPC ............ 607/92; 607/93; 607/89; 607/88; 606/15; 606/14; 606/13
(58) Field of Classification Search
USPC ............ 607/92, 93, 89, 88; 606/5, 14, 13
See application file for complete search history.

(56) References Cited

U.S. PATENT DOCUMENTS

| | | | |
|---|---|---|---|
| 4,786,812 A | 11/1988 | Humphreys | |
| 5,637,877 A | 6/1997 | Sinofsky | |
| 5,855,203 A | 1/1999 | Matter | |
| 6,443,147 B1 | 9/2002 | Matter | |
| 6,460,540 B1 | 10/2002 | Klepper | |
| 6,470,888 B1 | 10/2002 | Matter | |
| 6,551,346 B2 | 4/2003 | Crossley | |
| 7,159,590 B2 | 1/2007 | Rife | |
| 2002/0091424 A1* | 7/2002 | Biel | 607/88 |
| 2006/0130846 A1* | 6/2006 | Rife | 128/207.15 |
| 2008/0159908 A1 | 7/2008 | Redmond | |
| 2008/0257355 A1* | 10/2008 | Rao et al. | 128/207.14 |
| 2008/0306454 A1 | 12/2008 | Sikora | |
| 2009/0071484 A1* | 3/2009 | Black et al. | 128/207.14 |

* cited by examiner

*Primary Examiner* — Kinam Park
(74) *Attorney, Agent, or Firm* — Paul M. Denk

(57) ABSTRACT

A device delivers light within a patient using an inner cannula, fiber optics, LED along an endotracheal tube, ETT or tracheostomy tube or a strip with embedded LED adhered to an ETT. The inner cannula includes a tubular thin walled device that transmits light by fiber optics or delivers electrical power to an LED. The light passes along one or more fibers placed within the walls of the inner cannula for outward delivery of the light. The light affects the inside of the cannula, the area between the cannula and the ETT, the area outside the ETT, and into the tracheobronchial tree. The light delivers an antimicrobial effect into the upper airway of a patient. Alternatively, the light delivery device involves tubes and cannulas attaching to existing medical tubes and devices. Alternatively, a transparent strip of embedded LED secures to an existing medical tube.

8 Claims, 6 Drawing Sheets

TUBULAR DEVICE DELIVERING LIGHT AND RADIATION INTO A PATIENT

CROSS REFERENCE TO RELATED APPLICATIONS

This non-provisional application claims priority to the pending provisional application having a Ser. No. 61/210,515 and a filing date of Mar. 20, 2009 commonly owned by the same inventor.

BACKGROUND OF THE INVENTION

The present invention relates to tubular medical devices and more particularly to catheters and cannulas that deliver visible light, infra red light or radiation, ultraviolet light or radiation, and other radiation along the course of the catheters and to the tips of the catheters and cannulas when inserted within a patient. The present invention utilizes various wavelengths of light to reduce or to eliminate bacterial growth in the airways of patients.

A patient presents to a medical practitioner with a wide variety of symptoms. Generally the practitioner checks for life threatening symptoms or conditions and then shifts to more chronic ailments. Life threatening conditions generally affect the airway, breathing, or circulation. Circulation conditions receive various cardiac treatments. Acute and chronic respiratory failure frequently requires placement of breathing tubes into the trachea either trans-nasally, trans-orally, or directly in the trachea of a patient. The tube can then provide air flow to the lungs either by spontaneous respiration or upon a ventilator. Beyond respiratory conditions, tubes also see usage in treating digestive conditions where a component of the digestive track requires a supported reopening. Tubes used for respiratory or digestive conditions remain open and allow for air or digestive matter to pass through. However, tubes at times, provide an eddy at their ends where infection vectors or digestive matter may collect. Such vectors and matter lead to infections that require additional care.

Over the years, various tube sumps have entered the market and connect sumps to ventilation, tracheal, and endotracheal tubes among others. A prior invention, U.S. Pat. No. 6,460,540 of the Applicant, suctions material out from the upper airway. The tube sump has a flexible, elongated, hollow main body and then a plurality of separate clips or clamps attached to the main body. The hollow main body allows for suction to drain any infection vectors or digestive matter that accumulates above the endotracheal tube cuff when located in a patient's trachea. In the setting of life support tubes, such as endotracheal tubes "ETT" and tracheostomy tubes, the upper airway of a patient frequently becomes contaminated and colonized by bacteria.

Ventilator associated pneumonia, "VAP", a common medical illness, has high morbidity and mortality. VAP arises from micro and macro aspiration of contaminated secretions from the area of the pharynx and trachea. Methods to remove secretions from these areas and to reduce the microbiologic load have reduced the incidence of VAP as shown by various studies. Endotracheal tubes serve as tubular medical conduits through which oxygen, various gases, and medications pass while ventilating a patient. The proximal end of an ETT, outside of the patient, attaches to a ventilator, an oxygen tubing apparatus, or to an anesthesia machine for general anesthesia. The distal end of the ETT, inside of the patient, lies in the trachea and seals to the trachea by a circumferential air filled cuff which allows positive pressure ventilation of the patient. Contaminated and infected secretions tend to accumulate in the space above the cuff, at the cuff and below the cuff when an ETT occupies a patient's tracheobronchial tree. Treatments or effects that sterilize these areas would provide plenty of benefits to patients with a host of ailments. Furthermore, an ETT itself becomes colonized by infection internally along its luminal axis. Secretions retained within the luminal axis frequently obstruct airflow and the passage of suction catheters. Such a blockage of airflow can lead to life threatening artificial airway obstruction and occasionally requires removal of the life support tube and its replacement with a new tube.

Further, various prior art devices access the region of the patient's glottis and evacuate secretions from these areas. However, infection vectors may remain behind at the distal end of prior art devices. VAP occurs as a common complication of mechanical ventilation and it carries a high degree of morbidity, mortality and cost. Medical practitioners know that contaminated material in these areas migrates into the lungs around the endotracheal tube cuff and then causes pneumonia in patients. Further research has also shown that evacuation of these secretions and to some extent, decontamination of these secretions prevents VAP. Various wavelengths of light are known to suppress growth or kill microbes. The present invention provides an embodiment that decontaminates secretions using light emitting diodes or fiber optic light guides to conduct light into the airway.

A further alternate embodiment builds upon the prior art as it utilizes fiber optics upon a catheter or cannula to deliver light and select radiation to a location where secretions accumulate. This fiber optic energy delivery system then sterilizes, decontaminates, or otherwise reduces the microbial counts in the aero or digestive lumens or spaces of a patient. Transmission of various wavelengths of light into the desired space within a patient may reduce the likelihood or severity of infections from microbial colonization and contamination of the mucosa and accumulated secretions.

This embodiment of the invention includes a fiber optic delivery system that transmits antimicrobial wavelengths along a conduit parallel to an ETT or other medical tube within a patient. The conduit may be located internal or external to an ETT. This embodiment utilizing light and other radiation may be applied to or used with a tracheostomy tube, such as a light enhanced inner cannula. The unique feature of this embodiment of the invention is silica, fluropolymer, or plastic light guides, singular or bundled, bare or cladded, for delivering light within a patient to the location of greatest need. Though light diffusion or emission may occur from various alterations in the cladding, the present invention staggers the tips of the fiber optics in bundled applications or other tip treatments.

DESCRIPTION OF THE PRIOR ART

Tube sumps have been developed in many forms in the prior art. The U.S. Pat. No. 6,460,540 to Klepper has an endotracheal tube sump that included a suction tube, or catheter, used to evacuate material from the airway of humans. This suction tube connected to a suction generating device on one end and vacuumed material into the suction tube via one or more openings at the other end. This suction tube enters the upper airway of a patient through the mouth as it is attached to and follows an existing ventilatory support tube, or endotracheal tube, ETT. The suction tube has connectors that consist of circular clips. These clips are then attached to the suction tube as incomplete tubular structures that can warp around the ventilatory tube and advanced by sliding along the course of the ventilating tube. However, the tube and clips remain separate components that require mutual attachment prior to placement within a patient. Existing tubes do not deliver light and other radiation down the tube and into the patient.

The present invention overcomes the difficulties of the prior art. The present invention uses an improved cannula, cables, wires, and other linear devices to deliver electricity, light and other radiation within a patient. The present invention uses LED, fibers, fiber optics, wires, and other radiation conveying means, to locate a spot or a beam of light at a strategic location within a patient. The present invention has a preferred and two alternate embodiments that transmit light within a patient to neutralize microbes and other infection causing vectors.

SUMMARY OF THE INVENTION

The present invention provides an inner cannula system for an ETT but not for a tracheostomy tube. The inner cannula includes a generally tubular thin walled device that is inserted into the ETT. The inner cannula extends from the tip of the ETT, which enters a patient's trachea, and to an opposite end attaching to a ventilating source. The inner cannula permits utilization of an ETT adapter/connector, or a fitting connecting an ETT to the ventilator tubing in its first embodiment. Alternatively the inner cannula may have its own connecting method. The inner cannula also transmits energy, such as light, by fiber optic fibers in the second embodiment or delivers electrical power to an LED (light emitting diode) to operate a light source within and along a cannula or at the tip of the cannula. The fiber optic or LED may be integral with the cannula or may attached to the cannula. The fiber optic or LED may have single or multiple locations anywhere along the inner cannula. The energy or radiation, such as light, may pass along one or more fibers placed within the walls of the inner cannula. The fibers then deliver their light outwardly in all directions along the length of the fibers and from the tip of the fiber. The light energy therefore may affect the inside of the cannula lumen, the area between the cannula and the ETT, and the area outside the ETT itself as well as downward into the tracheobronchial tree.

In the second embodiment, the cannula has the fiber optic materials embedded in the cannula walls during extrusion at time of manufacturing. Alternatively, the fiber optic lines attach to or insert within the cannula walls before insertion into a patient. Further, the fiber optic materials pass through an existing aperture or follow an existing ETS or ETT with fiber optic devices to deliver an antimicrobial effect into the upper aero digestive tract. Such an ETS includes the prior art Endotracheal Tube Sump of the Applicant that passes from the mouth to the upper trachea.

There has thus been outlined, rather broadly, the more important features of the invention in order that the detailed description thereof that follows may be better understood and that the present contribution to the art may be better appreciated. In the preferred form, the present invention adds energy production and conductive properties of lines for delivery of radiation, particularly light wavelengths into a patient. The fiber optic strands and the LED generating sources exemplify light transmission and generating systems as components for this invention. However, the Applicant foresees that other conductive or transmittive method may be used and applied. Sensing, measuring and monitoring information about the medical status of a patient may be procured from these features of the invention. Additional features of the invention will be described hereinafter and which will form the subject matter of the claims attached.

Numerous objects, features and advantages of the present invention will be readily apparent to those of ordinary skill in the art upon a reading of the following detailed description of the presently preferred, but nonetheless illustrative, embodiment of the present invention when taken in conjunction with the accompanying drawings. Before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, the phraseology and terminology employed herein are for the purpose of description and should not be regarded as limiting.

It is an object of the present invention to provide a device and method of delivering radiation precisely to the tip of a cannula inserted within a patient.

It is another object of the present invention to provide a cannula that is removable separately from an ETT for cleaning or disposable.

It is another object of the present invention to avoid removing an emplaced ETT which prevents clogging and reduces infective colonization, contamination, and bio-film formation adverse to a patient.

It is another object of the present invention to provide for the production and conduction light energy into a patient.

It is another object of the present invention to provide fiber optic strands that avoid impaling a patient.

It is another object of the present invention to procure sensing, measuring and monitoring of various physiologic indices.

It is another object of the present invention to provide a tubular structure designed to fit inside an artificial airway.

It is another object of the present invention to provide for its ready removal and disposal, or cleaning and replacement.

It is another object of the present invention to incorporate light energy into the management of microbial contamination and colonization of the native and artificial airway It is another object of the present invention to allow suctioning of liquid/semi-liquid material from the mouth, throat, larynx and trachea of a patient.

It is another object of the present invention to guide along an existing ETT.

It is another object of the present invention to be inserted into a patient already attached to and positioned on an ETT.

It is another object of the present invention to inject or instill materials into the mouth, throat, larynx and trachea of a patient.

It is another object of the present invention to attach light sources which convey energy into the mouth, throat, larynx and trachea of a patient.

It is another object of the present invention to allow the placement of any diagnostic or therapeutic mechanism, energy source, optical device or monitoring means into the mouth, throat, larynx or trachea of a patient.

It is another object of the present invention to provide a conduit or other conducting apparatus for electric energy.

It is another object of the present invention to utilize conductive material to convey energy, such as light, along an ETS.

It is another object of the present invention to incorporate light, energy, or other radiation into a tracheostomy tube.

It is another object of the present invention to utilize fiber optic, LED, or other light and radiation transmission means to improve existing tracheostomy cannulas.

It is another object of the present invention to provide conductive elements that transmit and receive energy radiation.

It is another object of the present invention to allow conduction of light into the upper airway.

And, it is another object of the present invention to provide a new and improved tubular device delivering light and radiation into a patient that may be readily manufactured, easily setup, and operated at lower cost than existing devices.

Further objects and advantages of the subject invention will be apparent to those skilled in the art. These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated a preferred embodiment of the invention.

BRIEF DESCRIPTION OF THE DRAWINGS

In referring to the drawings.

The same reference numerals refer to the same parts throughout the various figures.

DETAILED DESCRIPTION OF THE INVENTION

The present invention provides a device that conveys light and other radiation through an elongated conduit placed along a tube to its tip, to one or more points along the course of the device or conduit, and to the entire length of the device or conduit. Tracheostomy inner cannulas have existed for years as a removable component that prevents material buildup internal to a patient. This invention adds fiber optics, LED sources or similar energy conducting and generating methods to a tracheostomy inner cannula to convey the beneficial effects of light into the trachea of a patient. Like an ETT, the light energy, for example, may be transmitted superiorly above the tracheostomy tube toward the vocals cords, to the areas between the tracheal stoma and the tip of the tracheostomy tube and into the tracheobronchial tree itself of a patient. As with an ETT cannula, this application of fiber optic or LED light, and like technology may take various configurations, with any location, pattern, and combination of technologies. The preferred and alternate embodiments of the invention, fiber optic or LED light generation, direct light to all areas through out the course of travel of an ETT; that is from the oral cavity to the trachea and including the inside of the ETT and inner cannular lumen.

Figures 1, 2A, 2B:
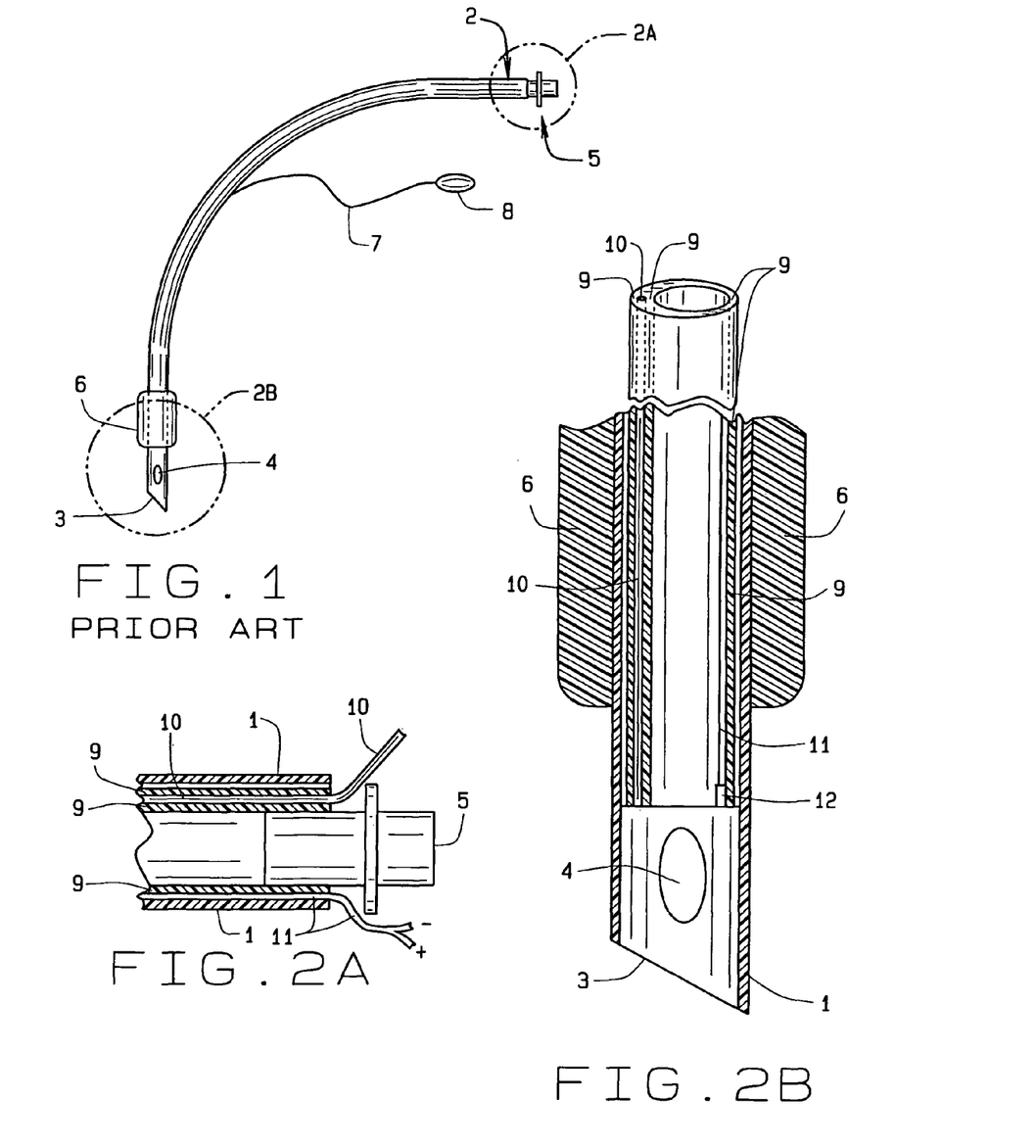
FIG. 1 illustrates a prior art endotracheal tube with cuff and connector to a ventilating source.
FIG. 2A shows light transmitting means locating proximate the connector to a ventilating source.
FIG. 2B shows the light transmitting means terminating outwardly of the cuff particularly, the relationship between the ETT and the inner cannula.

An existing endotracheal tube is shown in FIG. 1. The ETT has a flexible elongated tube 1 with an end 2 that connects to other equipment and an opposite tip 3. The hollow tube conveys fluids and gasses along its length from the end to the tip. The end has a generally round opening while the tip has a round opening with an aperture 4 upon the tube, at a right angle to the tip's opening. The end receives a ventilating connector 5, known in the art. Proximate the tip and generally above the aperture, the ETT has a cuff 6 that expands, generally with air introduced by a line 7 and a bulb 8.

The present invention appears initially in FIG. 2A which depicts the intra-tracheal aspect of the ETT and the external ventilating portion 5 at the end 2. This view of the ETT's intra-tracheal portion shows the relationship between the ETT 1 and an inner cannula 9 coaxial with the ETT. This embodiment includes a fiber optic application 10, shown traveling lengthwise within the wall of the inner cannula. Though shown traveling straight and longitudinally in this figure, the Applicant foresees that the fiber optic application may travel in a spiral, helical, or sectional path within the inner cannula. Proximate the ventilating portion 5, the preferred embodiment has a power source 11 for a light emitting diode as later described. The power source includes a battery with a line to the LED and an energized electrical line from an outside electrical source, such as transformed utility service. In the LED embodiment, electrical power will travel by wire to the LED located within, or immediately adjacent to, the inner cannula 9.

In more detail opposite the end 2, FIG. 2B shows the vicinity of the tip 3. The tip has a slight bevel to aid insertion of the ETT within a patient. Upwardly from the tip, the ETT has its aperture 4 for withdrawing fluids and matter through the tube and providing ventilatory airflow. Upwardly from the aperture and upon the exterior of the tube, the cuff 6 has a generally cylindrical form with a central chamber to admit the ETT. The cuff stands ready for inflation or deflation by the bulb 8 as previously described. Within the tube and inside of the cuff, the inner cannula 9 extends to the aperture. Upon one wall of the inner cannula, a fiber optic application 10 extends to the tip of the cannula. The tip of the fiber optic then releases light energy proximate the aperture. Alternatively, the fiber optic may release its light, energy, or radiation, anywhere or entirely along its course. Opposite the fiber optic, the LED embodiment has a line delivering electrical power from the source 11 to the LED itself 12 locating at the tip of the cannula. The LED then emits its light proximate the aperture. Further, the LED element 12 may also deliver light energy at various points along the inner cannula with subsidiary elements. Generally, the inner cannula 9 including fiber optic application or LED elements, functions as a liner within the ETT. The present invention delivers blue wavelength light either by fiber optic entrainment or by miniaturized LED for infection suppression and prevention. The fiber optic lines and LED generally provide specific blue light wavelengths of approximately 400 to approximately 475 nm and have a size as small as approximately 1×0.6×0.25 mm. The fiber optic lines and LED literally fit within the wall of the inner cannula.

Figures 3, 4:
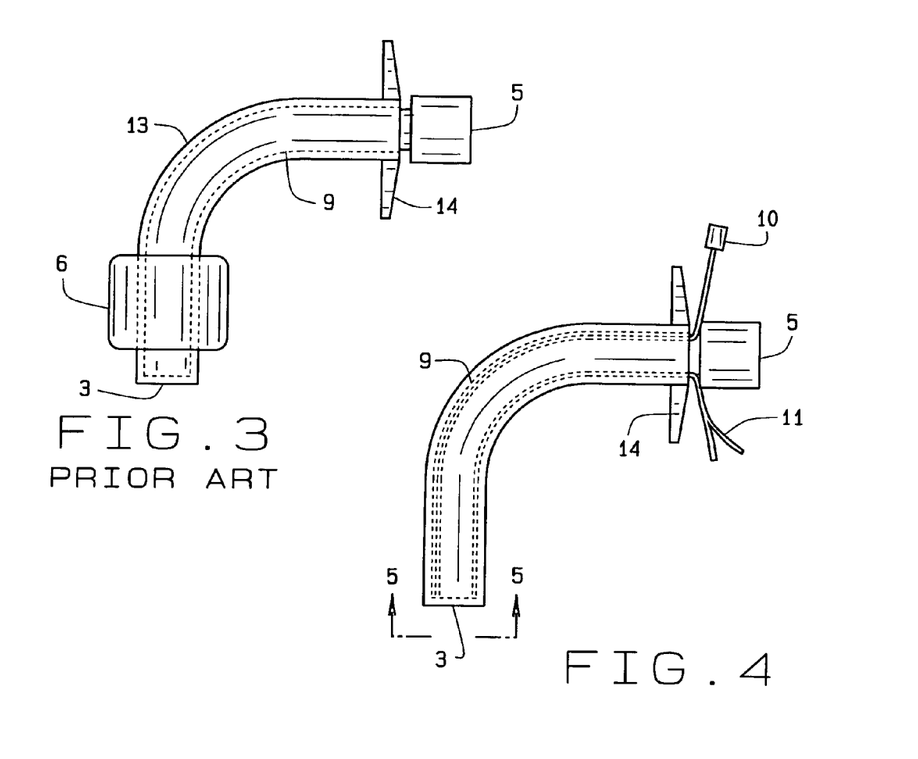
FIG. 3 shows a prior art tracheostomy tube with an external end that connects to a ventilating source and an intratracheal portion along with an inner cannula.
FIG. 4 provides an inner cannula with fiber optic and LED embodiments.

Returning to the prior art briefly, FIG. 3 shows a standard tracheostomy tube 13 with an external end 14 which connects to the ventilatory means 5 and an opposite intra-tracheal portion 3 with a nearby cuff 6. An inner cannula 9 is shown lining the length of the tracheostomy tube 13.

FIG. 4 provides a tracheostomy tube 13 with an inner cannula 9 as in the present invention. This inner cannula supports both embodiments of the invention, particularly the fiber optic application 10 and the LED 12 with its power source 11. The power source locates proximate the external end 14 while the fiber optic and LED power lines extend along the length of the tracheostomy tube 13. Though the fiber optic and LED power lines are shown extending lengthwise within the inner cannula, the Applicant also envisions that the fiber optic and LED power lines may follow spiral, helical, or sectional paths.

Figure 5:
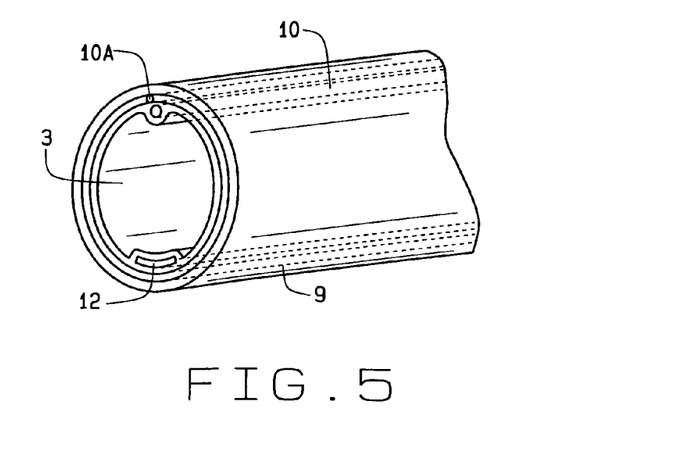
FIG. 5 describes a detailed view of a tracheostomy tube with the inner cannula in place along with fiber optic and LED elements.

And, FIG. 5 shows a detailed view of the intra-tracheal end 3 of the tracheostomy tube 13 with the inner cannula 9 in place. The inner cannula has the tips shown of the embodiments of the fiber optic application 10 and of the LED element 12.

Figures 6, 7:
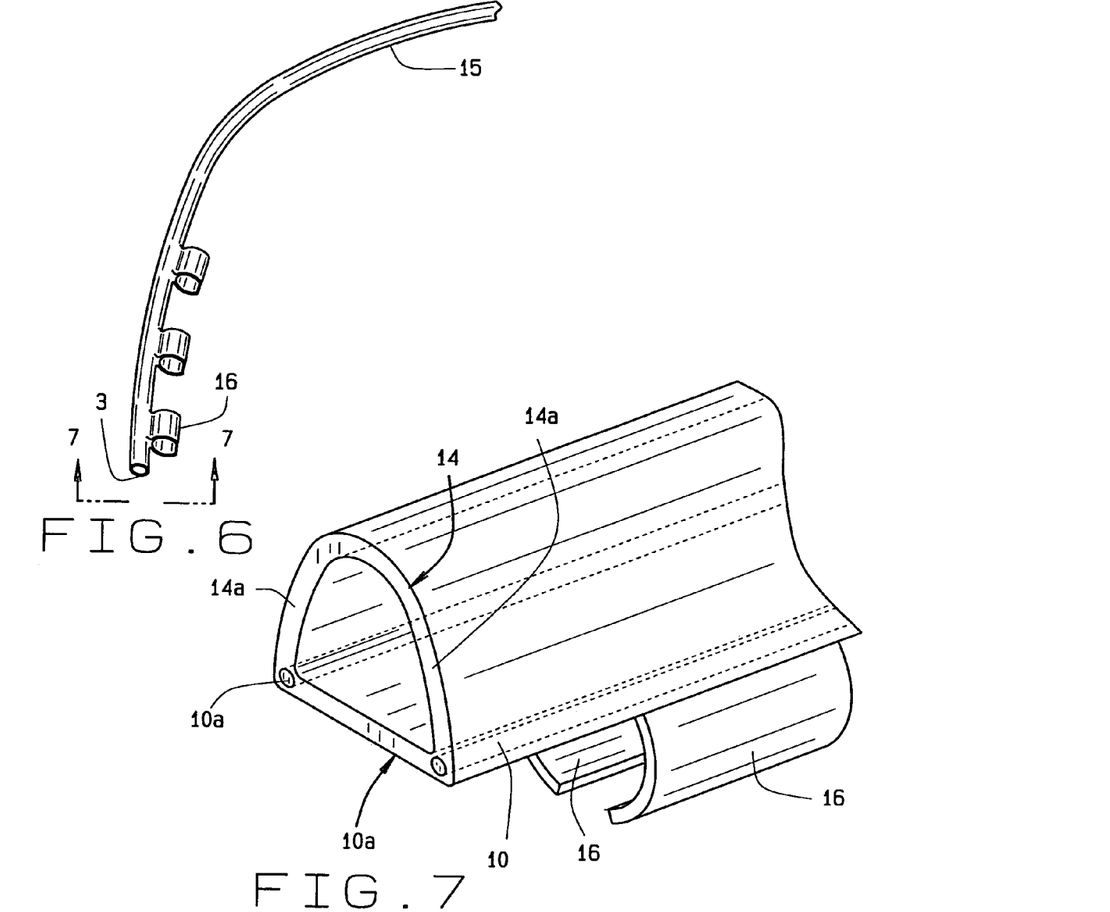
FIG. 6 shows an ETS catheter with light conductive means therein and with clips which guide the catheter along the course of the ETT.
FIG. 7 provides a detailed view of the tip of the present invention here with the light conductive means visible before insertion inside a patient where the present invention transmits light energy from the source to the suction end or tip of the catheter.

The embodiment of the fiber optic application appears in more detail with FIG. 6 beginning with an existing tube sump of the Applicant as in U.S. Pat. No. 6,460,540. The tube sump has a tube like catheter 14 that generally flexes and bends and has two opposite ends. Upon one end, the catheter has a fitting 15 for connecting the tube sump to a suction line or other medical device. And on the opposite end, the catheter has an open tip 3 that allows for collection and withdrawal of secretions and other matter through the catheter. Because the catheter flexes and bends, the catheter may deflect upon the structures of a patient's pharynx and miss insertion into the trachea, esophagus, or other desired organ. The patented tube sump of the Applicant provides at least one, preferably two, clips 16 separately made from the catheter. Each clip generally has an interrupted figure eight like cross section with a small end and an opposite large end. The large end has two jaws that allow the clip to grip ETT or other tubular devices as selected by the medical staff. The small end has two lesser jaws that deflect outwardly and slip upon the catheter. In a typical application, shown in FIG. 6, one clip is located proximate the tip 3 and additional clips are located within one third the length of the catheter away from the tip. The clips can be relocated by the medical staff by manipulating the lesser jaws of a clip's small end.

The prior art tube sump utilizes separate clips that require the medical staff to locate the clips upon the catheter and that may slide somewhat when lubricated by bodily fluids upon insertion within a patient. In an alternate embodiment, also shown in FIG. 6, a tube sump includes integral clips that prevent the sump from sliding along a catheter 14. The alternate tube sump has at least two integral clips 16, here shown as three. These clips 16 have a generally round cross section and a C like shape with the opening of the C like shape being approximately 90° to the catheter portion of the tube sump.

The present invention involves the conveyance, conduction, or transmission of bactericidal or bacteriostatic energy forms into the region of the patient's mouth, pharynx, supraglottis, subglottis, trachea, and the like. Various wavelengths of light suppress and kill microbes. Light can be conveyed into this area by utilizing the catheter itself or specific light guiding methods such as glass fibers or polymer optical fibers. Polymer optical fibers transmit light by conduction because the fibers have proper internal and external treatments to control reflection and loss of light at the wall interface of the fiber. Generally, an external light source, as at 17, in FIG. 5 which will be further discussed hereinafter, produces light which is then directed into the light conductive apparatus and along the ETS device into the patient. The light can be allowed to diffuse at any level and in any direction in relation to the ETS catheter main axis. The Applicant also foresees generating light within the ETS itself by using miniaturized light sources, such as LED, as later described.

An alternate embodiment of this ETS improvement, for usage with the prior patented device of the Applicant, includes a fiber optic strand embedded in the wall of the catheter 14, attached to the catheter, extruded at manufacture, and like methods of manufacture. The light guide, as at 10, extends through the main body of the suction catheter and projects light in various directions depending on the intended application. The light may be directed and its transmission manipulated by a variety of methods and treatments to the fiber tip as at 10a, in FIG. 5, the insulating cover, or the material through which the fiber extends. The stated energy conducted is visible blue light but may also be other light or radiation, from any conceivable generating method.

The primary purpose of this embodiment is projecting bactericidal light wavelengths into the upper airway of an intubated patient to decontaminate the area of accumulated material. This embodiment results in the diffusion of light into the adjacent endo-tracheal tube, killing or suppressing bacteria within the endotracheal tube lumen of a patient.

Figures 9, 10:
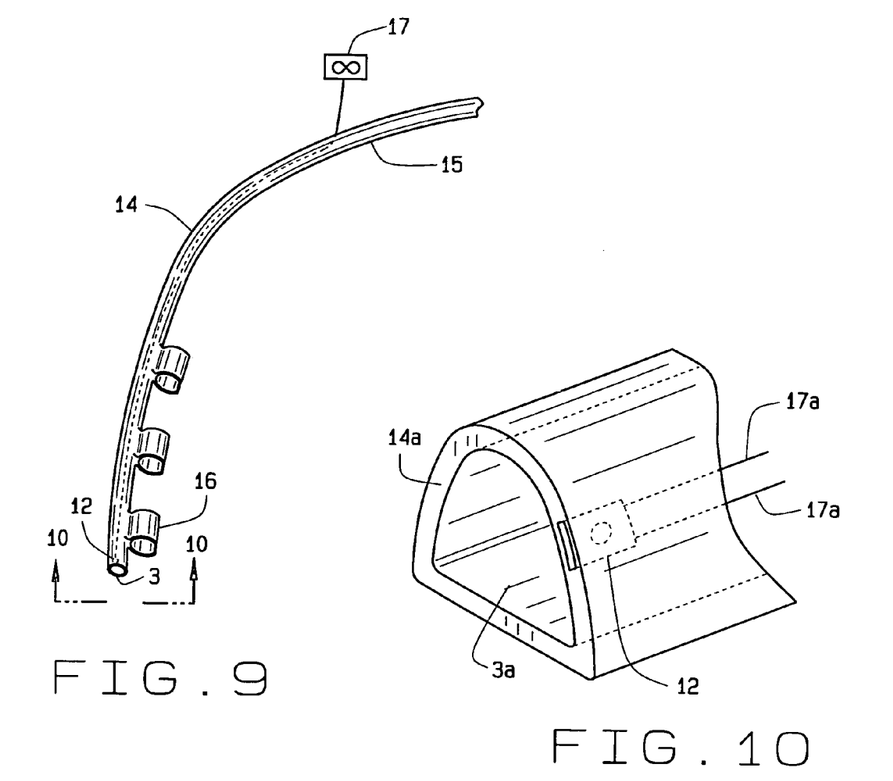
FIG. 9 shows another ETS catheter with energy delivery means and an LED proximate the tip and with clips which guide the catheter along the course of the ETT.
FIG. 10 describes a detailed end view of an ETS with an LED at the tip.

FIG. 6 as further described from above demonstrates a fiber optic element 10 or, as further shown in FIG. 9, a bundle conductive device with a light source 17 locating outside the patient. This embodiment transmits light energy from the source along the catheter 14 to the suction end 3 of the catheter. The light then reaches a desired internal region of a patient.

FIG. 7 shows another detailed view of the suction tip 3 of an ETS catheter 14. The fiber optic elements 10 are shown extending within the suction catheter's walls 14a and terminating their ends 10a at the suction tip 3 itself. The ends 10a deliver the light at the point where the suction tip collects the matter and fluids from within the patient, a prime infection location.

Figure 8:
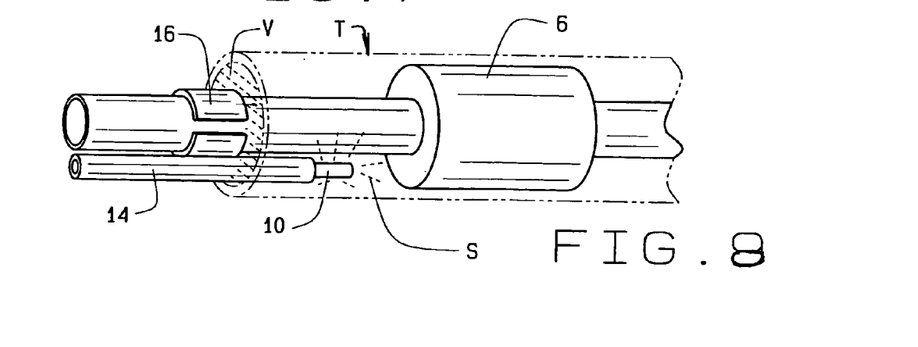
FIG. 8 demonstrates the anatomical relationship of the ETT, ETS, and the subglottic space wherein the present invention locates and deploys its light conductive means.

And, FIG. 8 shows the anatomical relationship of the ETT 1, ETS shown by its catheter 14, and the surrounding subglottic space as at S. The subglottic space includes the trachea T of a patient here shown as a longitudinal section and vocal cords V here shown at the end of the trachea. The vocal cords are shown spread apart with the ETT 1 and clips 16 passing through them. The fiber optic element 10 then conveys its light along the path of the ETS 14. When the medical staff locates the ETT at its desired location, the staff inflates the cuff 6 against the internal surfaces of the trachea. The ETT 1 then allows for inhalation and exhalation of the patient.

The alternate embodiment of the LED involves the utilization of LED, or light emitting diode, or substantially similar energy sources, to induce a germicidal effect in the upper airway of a patient. LED light sources may be attached to, molded into, or implanted in a catheter during the production of the ETS to foster this effect. As above, various light wavelengths have antibacterial effects and light directed at various points along the course of the ETS has benefits to the patient. The LED may locate anywhere in the ETS to generate light in the desired area. The alternate embodiment of a catheter based LED light source insertion applies beyond the ETS devices shown. This alternate embodiment foresees various devices that inserting an LED source into the mouth, pharynx, nose, sinuses, larynx, supraglottic and subglottic spaces, and the trachea of a patient. The LED light projection into the upper airway and contiguous structures though requires a LED generating source and at least one wire to transmit power to the LED from a source, generally external to the patient. This embodiment includes a LED lamp directly wired to a power source to more elaborate configurations involving LED holders, lens systems, and rigid or flexible probes or conduits.

This alternate embodiment includes a miniature LED implanted or embedded at or near the suction terminus, or end 3, of an ETS 14 as shown in FIG. 9. This embodiment utilizes an external power source as at 17 that delivers electrical power, as shown in FIG. 10, through at least one wire, as at 17a, to an LED 12. The power source wires 17a generally run within the wall 14a of the suction catheter 14 and outward, as shown in FIG. 9, from the connector end as at 15 to allow attachment to a suitable power source 17. The LED unit 12 may be located anywhere along the length and path of the catheter. Though one LED is shown, the Applicant foresees additional LED units to suit various applications.

The ETS, or endotracheal tube sump, 14 represents the body of the device. The suction catheter tip 3 removes material from the upper airway of a patient while the clips 16 guide the catheter 14 along an endotracheal tube. Advancement of the catheter along the curvature of the indwelling ETT conveys the suction tip 3 with the LED 12 into to the subglottic space S as previously shown in FIG. 8. The subglottic space S includes the trachea walls T circumferentially, an ETT cuff 6 inferiorly and the vocal cords V superiorly. Here, the energy source includes an LED light source 12 either attached to or embedded in the suction tip 3 as shown in the detailed view of FIG. 10. Any necessary wires 17a may travel along the suction catheter 14. In this embodiment, connection of a power source 17 to the wires 17a yields light energy within the subglottic and surrounding spaces S. The LED 12 are generally located in the catheter wall 14 and proximate the tip 3 of the catheter and generally illuminate a suction lumen as at 3a and the surrounding adjacent patient spaces.

Figure 11:
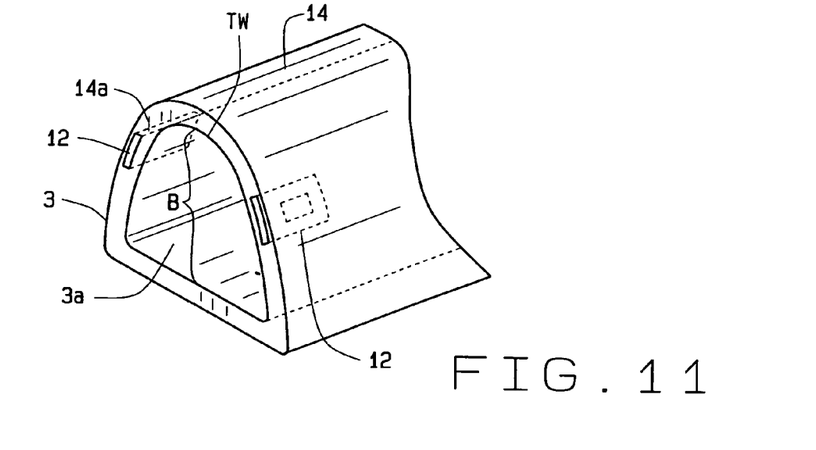
FIG. 11 describes another detailed end view of an ETS with a pair of LED at the tip.

Viewing the end 3 in more detail, FIG. 11 shows a suction lumen 3a with two flanking LED 12. The LED are generally embedded within the wall 14a of the catheter. The catheter wall is approximately 0.7 mm in thickness as at TW with a suction lumen, as shown in the FIG. 11 embodiment, approximately 3 mm in height as at B. The suction lumen has a generally triangular shape. LED embedded in the catheter wall generally have a thickness less than 0.6 mm and a width much less than 3 mm.

Figure 12A:
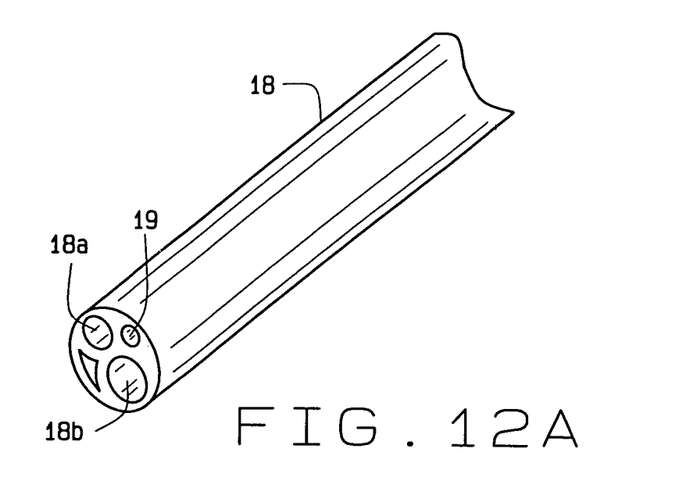
FIG. 12A shows a dual lumen tube with light conducting means locating proximate the juncture of the lumens and FIG. 12B shows the dual lumen tube with one lumen cut back from the other lumen and a plurality of LED spaced along the tube.
Figure 12B:
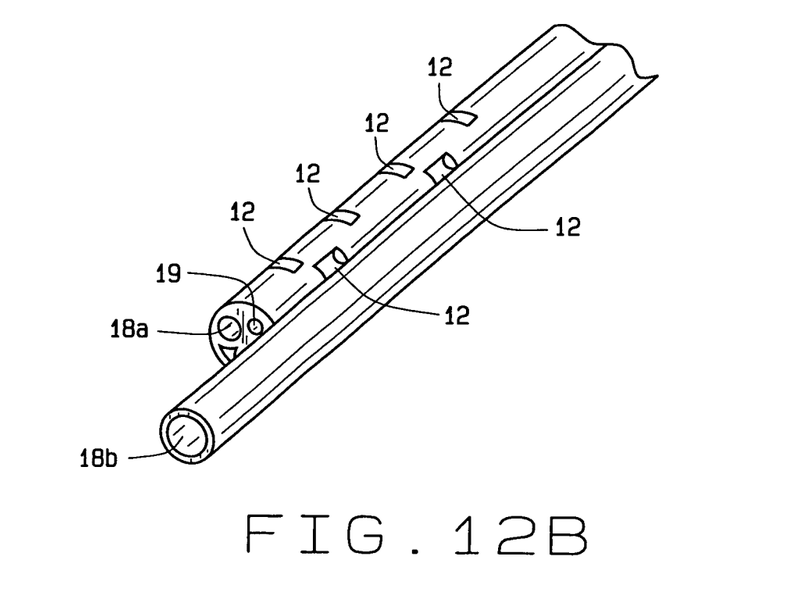

FIG. 12A shows a dual lumen tube 18 with light conducting means 19 locating proximate the juncture of the lumens 18a, 18b. The wall of the tube 18 enwraps the two lumens 18a, 18b however the diameters of the lumens being less than that of the tube provides a chord like space between the lumens and the tube. The chord like space has sufficient height to admit at least one light conducting means 19 which includes fiber optic and LED with wiring as previously described. Then FIG. 12B shows a generally similar dual lumen tube 18 with one lumen 18a cut back from the other lumen 18b and a plurality of LED 12 spaced along the tube. Here, the other lumen 18b operates as a suction catheter. The first lumen 18a has various apertures thereon. The tube may include additional LED or provide markings or slits for bending of the tube 18 for installation within a patient.

Figure 13:
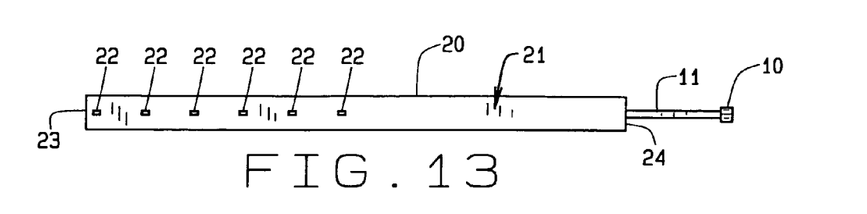
FIG. 13 shows a top view of an embodiment of a strip including LED.

Another alternate embodiment of the invention appears in a top view of FIG. 13 having the form of a strip 20. This embodiment seeks to modify an endotracheal tube with an integral or attached light source preferably where the light source has visible light generating capabilities. The strip is generally planar, elongated, and of thin cross section. The strip has a width of approximately 1 mm to approximately 10 mm, a thickness of approximately 0.1 mm to approximately 1.5 mm, and a length of approximately 200 mm to 300 mm, excluding electrical or fiber optic leads. The strip is generally a narrow rectangle as shown with a distal end 23 and an opposite proximal end 24 from which extend the electrical or fiber optic leads as at 11. The leads communicate to a power source through a compatible connector 10. The strip 20 has a top surface 21 that extends for its length and that generally locates outwardly from an ETT when installed as later shown in FIG. 16. The top surface has a plurality of light sources 22 spaced inwardly from the distal end 23. The light sources upwards of 15 individual units. The light sources are preferably light emitting diodes, LED, or alternatively fiber optic emitters. The light sources receive power from wiring between them that runs back to the leads as later shown in FIG. 15. The light sources emit visible light, and preferably blue light of the wavelengths previously described. The light sources are preferably multidirectional or alternatively unidirectional. Though FIG. 13 shows light sources in line and at a regular interval of approximately 1 mm to approximately 30 mm, the light sources may also be placed out of line, staggered, at an irregular spacing, or along the entire length of the strip and like arrangements to optimize treatment of the patient.

Figure 14:
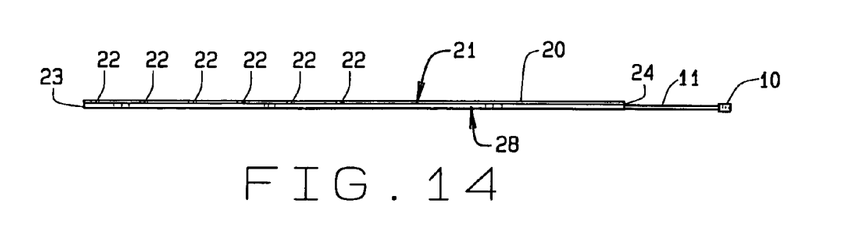
FIG. 14 is a side view of the strip embodiment.

FIG. 14 then shows the strip 20 from the side, generally with an edge along its length. The strip has its thickness, approximately 0.1 mm to approximately 1.5 mm, much less than its width approximately 1 mm to approximately 10 mm as previously shown. The strip has its light sources 22 spaced along its length, generally concentrating towards the distal end 23. The distal end inserts deeply into the patient, while the opposite proximal end locates more towards the head of the patient. The leads 11 extend from the proximal end and terminate in their connector 10. As before, the strip has its top surface but it also has an opposite bottom surface 28. The bottom surface generally secures the strip to an ETT during installation and usage as later described.

Figure 15:
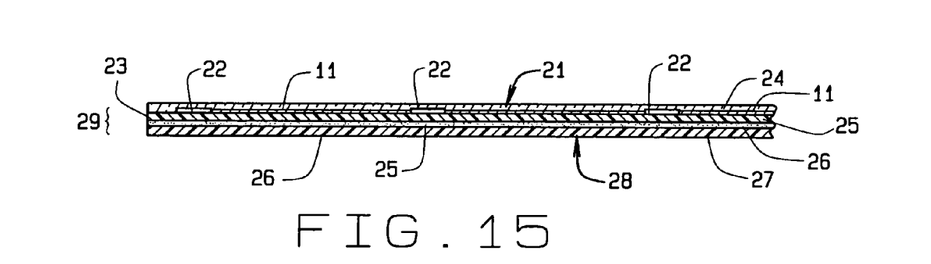
FIG. 15 is an enlarged sectional view of the strip embodiment.
Figure 16:
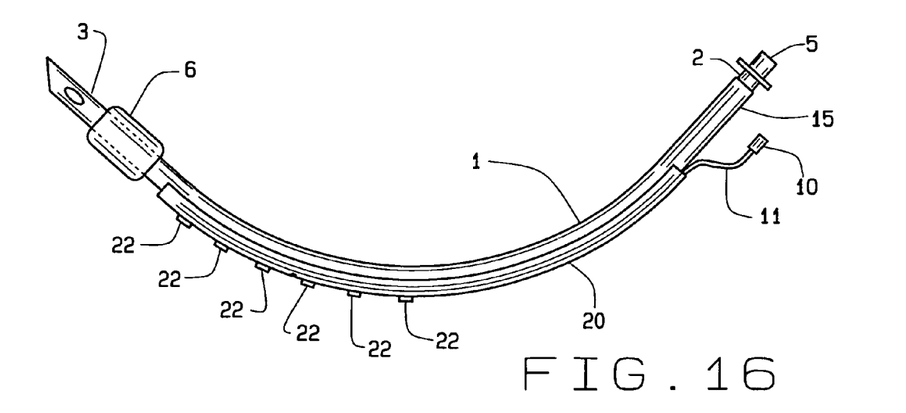
FIG. 16 illustrates deployment of the strip embodiment upon an endotracheal tube.

Turning to the construction of the strip in FIG. 15, the strip has its thickness as at 29. The construction begins with the top surface 21 that includes an encapsulant 24 of optical grade that contains the light sources 23 and wiring while protecting them from moisture, bodily fluids, and other hazards encountered during usage. The encapsulant may include acrylic, EVA resins such as Elvax® from DuPont of Wilmington, Del., PVB sheets also from DuPont, and PV5300 sheets also from DuPont. The encapsulant is generally planar with the length and width of the strip as previously described. Beneath the encapsulant, the strip has a base 25, or substrate, that is preferably transparent and alternatively opaque. The base provides form and partial rigidity to the strip, particularly during manufacturing and shipping. Beneath the base opposite the encapsulant, the strip has a securing layer, as at 26, that secures the strip to an ETT during usage as shown in FIG. 16. The securing layer includes adhesives, cohesives, magnets, glues, resins, epoxies, and the like. Beneath the securing layer, the strip has a release liner 27 that extends for the length and the width of the layer 26 generally the length and width of the strip. The release liner covers the securing layer to prevent premature attachment of the strip, such as to manufacturing equipment, its packaging, medical equipment, and the like, prior to usage in a patient. The release liner lightly adheres to the layer so that a user may readily remove it and expose the layer for placing the strip upon an ETT. Outwardly from the securing layer, the release liner forms the bottom surface 28 of the strip. Alternatively, when a pressure sensitive adhesive is used for the securing layer, the strip omits a release liner.

Then FIG. 16 shows the strip 20 installed upon an ETT ready for insertion into a patient. As before, an ETT has a flexible elongated tube 1 with an end 2 that connects to other equipment and an opposite tip 3 that inserts into a patient. The hollow tube conveys fluids and gasses along its length from the end to the tip. The end has a generally round opening while the tip has a round opening with an aperture upon the tube, at a right angle to the tip's opening. The end receives a ventilating connector 5, known in the art. Proximate the tip and generally above the aperture, the ETT has a cuff 6 that expands, generally with air introduced by a line. The ETT receives the strip 20 as shown along its length with the wiring 11 terminating at its connector 10 proximate the end 2 in the section as at 15. A user removes the strip 20 from its packaging and then detaches the release liner 27 exposing the securing layer. The user then presses the securing layer upon the exterior of the ETT above the cuff 6 towards the end 2. The strip generally stops at least 25 mm from the end of the ETT and has its wiring 11 extending freely for connection to a power source whether electrical or fiber optic.

One application of the strip 20 secures the strip to the greater curvature of an ETT at time of insertion. The strip runs from the proximal aspect of the inflatable cuff 6 to the external connector portion of the ETT, not shown. Then the connection provides external DC power that is cycled, pulsed, or continuous, as selected by the treating staff. This application illustrates that the strip 20 has a bend radius in excess of approximately 150 mm such that the strip has flexibility. As previously described, the base 25 and encapsulant 24 cooperate so that the strip bends. In this application, the strip may remain upon an ETT for up to 14 days or until removal of the ETT from the patient.

In another application, the strip 20 has a curled form similar to a tube or liner 30 that is then formed into a tubular device through simultaneous extrusion, co-extrusion, extrusion, lamination, and like manufacturing practices. In this tubular application, the liner 30 is then inserted into a prior art ETT. The liner then serves as a carrier of blue light into the upper airway of a patient, including the trachea. Secondarily, the liner serves as an inner cannula that can be removed from the ETT thus reducing airway contamination and accumulation of biofilm, as shown at 9 in FIG. 2B. In this application, the liner may have a collection of light sources 22 proximate its distal end 23 included within an engineered encapsulation. Alternatively, the strip may have a backing with at least one miniaturized reflective element that projects light downwardly through a tracheal lumen. During usage, the tip 3 of an ETT is generally 20 mm to 50 mm from the main division of the right and left bronchi. Alternatively, the liner may be manufactured using one or more strips wrapped into a tubular form as extruded. This liner may be produced as a reel with a repeating pattern of strips. The strips in this embodiment have a generally thin and malleable construction to aid in wrapping. This application further projects light energy circumferentially to defeat bacterial colonization outside of an ETT. During usage, select light sources may generate excessive heat within a patient. Heat dissipation may be provided through pulsing the power to the light sources or through a thermally conductive base 25.

The strip embodiment of the invention also sees use for tracheostomy patients. These patients have an opening in their trachea that communicates externally for breathing. Generally tracheostomy tubes have a disposable inner cannula that removes readily from the tracheostomy tube, such as after detection of contamination. Often bacteria colonize the respiratory tract of tracheostomy patients. The strip 20 with its light sources 23 generally blue, can attach to an existing tracheostomy cannula, generally upon the distal end. The strip attaches to a cannula similar to attaching to an ETT as described above. Illumination of the light sources then lessens the contamination of the cannula which allows for longer duration placement of the cannula in a patient.

The invention has been described herein with the reference to a preferred embodiment and certain alternate embodiments. It is understood that obvious variants thereon will become apparent to those skilled in the art. The invention is not to be considered as limited thereto. From the aforementioned description, various tubular devices to deliver light within a patient have been described. The devices are uniquely capable of deliver light to the tip of a sump or catheter when placed within a patient. The devices may be manufactured from many materials, including but not limited to, polymers, polyethylene, polypropylene, nylon, ferrous and non-ferrous metals and the alloys, and composites.

As such, those skilled in the art will appreciate that the conception, upon which this disclosure is based, may readily be utilized as a basis for the designing of other structures, methods and systems for carrying out the several purposes of the present invention. Therefore, the claims include such equivalent constructions insofar as they do not depart from the spirit and the scope of the present invention.

I claim:

1. A device for delivering light and other radiation through an endotracheal tube within a patient for medical treatment, and for suppressing infectious vectors, the patient having an endotracheal tube placed therein in preparation for treatment, comprising:

an endotracheal tube, said endotracheal tube having an inner end and an outer end;

a flexible cylindrical tube formed as an inner cannula and having inner and outer walls, said cylindrical tube having ends, one end of the cylindrical tube provided for locating within the endotracheal tube and in proximity with its inner inserted end, the opposite end of the cylindrical tube locating near the outer end of the endotracheal tube, said cylindrical tube capable of being inserted or removed from the endotracheal tube, during its usage, at least one lumen, said lumen having opposite ends, said lumen being embedded within the cylindrical tube, one end of said lumen locating proximate the inner end of the cylindrical tube, and the opposite end of said lumen extending from the cylindrical tube and approximate end of the endotracheal tube for connection with at least one radiation delivery unit for delivering light to said fiber optic for releasing light energy through the cylindrical tube;

a second energy transmitting line provided within the wall of the cylindrical tube an extending from exterior of the endotracheal tube to the inserted end of the cylindrical tube, at least LED to provide for further transmission of light from the inner inserted end of the endotracheal tube during treatment of a patient;

said fiber optic line delivering light radiation interiorly of the patient during treatment, and said light emitting diode emitting one of visible light, inferred light, and ultraviolet light into the patient during treatment;

wherein said cylindrical tube and its embedded fiber optic line and energy transmission line are readily removable from the endotracheal tube and the patient to facilitate cleaning, replacement, or disposal;

said endotracheal tube adapted to provide suction of liquid and semi-liquid material through the located cylindrical tube during application to suck liquid and semi-liquid material from the mouth, throat, larynx and trachea of the patient;

and said cylindrical tube adapted to attach within the endotracheal tube for their combined insertion into a patient during usage, and wherein said cylindrical tube allows for the injection or delivery of materials into the mouth, throat, larynx and trachea of the patient during usage, and wherein said cylindrical tube allows placement of any diagnostic mechanism or therapeutic mechanism, other energy source, optical device, surgical instrument, or other monitoring means into the mouth, throat, larynx or trachea of a patient; and wherein said flexible cylindrical tube removably located within the endotracheal tube providing for energization of the radiation delivery units for inspection and treatment of a patient during usage.

2. The light and other radiation delivery device of claim 1 wherein said device monitors and measures various physiologic indices of a patient.

3. The light and other radiation delivery device of claim 1 further comprising:
   said tube adapted to suction liquid and semi-liquid material from the mouth, throat, larynx and trachea of a patient.

4. The light and other radiation delivery device of claim 1 further comprising:
   said radiation delivery units receiving energy through conductive materials including one of copper wiring, aluminum wiring, or fiber optic lines.

5. The light and other radiation delivery device of claim 4, and wherein there are a plurality of light emitting diodes provided spacedly along the length of the radiation delivery unit to provide the delivery of its radiation along the length of the flexible cylindrical tube locating within the endotracheal tube of said device for delivering light and other radiation within a patient.

6. A device delivering light and other radiation along an endotracheal tube within a patient for medical treatment, and for suppressing infectious vectors, the patient having an endotracheal tube placed within the patients airway in preparation for treatment, comprising:

an endotracheal tube, said endotracheal tube having an inserted end, that locates within the patient, and an outer end, that extends outside of the patient;

an elongated strip having a top surface, an opposite bottom surface, a distal end for insertion into a patient, an opposite proximal end, a plurality of radiation sources proximate said distal end, said radiation sources in communication with conductive materials, said strip adapted to attach to the endotracheal tube externally thereof, said plurality of radiation sources including one of a light emitting diode, a fiber optic line, a light emitting diode capable of emitting blue light for managing microbial contamination and colonization in a native airway of a patient; and said strip having a base, wiring provided through said base and in communication with said plurality of radiation sources, a transparent encapsulate bonding with said plurality of radiation sources and said wiring to encapsulate said radiation source and wiring to the base, said wiring upon the base in communication with said plurality of radiation sources, a transparent encapsulant bonding said plurality of radiation sources and said wiring within the base, a securing layer upon said base opposite said encapsulant, said securing laying comprising one of an adhesive, cohesive, glues, resins, and epoxies, a release liner provided upon said securing layer, whereby said release liner may be removed and the strip applied along the length of the endotracheal tube to provide a radiation source for treatment of the patient when the endotracheal tube is inserted within the patient during treatment, and an energy source is applied to the outer end of the wiring to provide the delivery of energy such as electricity and light to the radiation source during treatment.

7. The light and other radiation delivery device of claim 6 further comprising:
   said plurality of radiation sources including one of a light emitting diode, a fiber optic line, an incandescent bulb, or a fluorescent bulb.

8. The light and other radiation delivery device of claim 7 further comprising:
   said light emitting diode thus emitting blue light for managing microbial contamination and colonization in a native airway of a patient or an artificial airway supplied for a patient.

* * * * *